United States Patent
Murry et al.

(10) Patent No.: US 9,527,813 B2
(45) Date of Patent: Dec. 27, 2016

(54) PROCESS FOR THE SYNTHESIS OF (+) AND (−)-1-(3,4-DICHLOROPHENYL)-3-AZABICYCLO[3.1.0]HEXANE

(71) Applicant: Euthymics Bioscience, Inc., Cambridge, MA (US)

(72) Inventors: Jerry A. Murry, Newbury Park, CA (US); Edward G. Corley, Freehold, NJ (US); Feng Xu, Staten Island, NY (US); Bryon Simmons, Princeton, NJ (US)

(73) Assignee: EUTHYMICS BIOSCIENCE, INC., Cambridge, MA (US)

(*) Notice: Subject to any disclaimer, the term of this patent is extended or adjusted under 35 U.S.C. 154(b) by 0 days.

(21) Appl. No.: 13/945,605

(22) Filed: Jul. 18, 2013

(65) Prior Publication Data

US 2014/0163240 A1    Jun. 12, 2014

Related U.S. Application Data

(63) Continuation of application No. 13/366,211, filed on Feb. 3, 2012, now abandoned, which is a continuation of application No. 13/207,279, filed on Aug. 10, 2011, now abandoned, which is a continuation of application No. 12/782,705, filed on May 18, 2010, now abandoned, which is a continuation of application No. 11/740,667, filed on Apr. 26, 2007, now abandoned.

(60) Provisional application No. 60/796,097, filed on Apr. 28, 2006.

(51) Int. Cl.
| | |
|---|---|
| *C07D 209/52* | (2006.01) |
| *C07C 211/29* | (2006.01) |
| *C07C 215/38* | (2006.01) |
| *C07C 255/46* | (2006.01) |

(52) U.S. Cl.
CPC .......... *C07D 209/52* (2013.01); *C07C 211/29* (2013.01); *C07C 215/38* (2013.01); *C07C 255/46* (2013.01)

(58) Field of Classification Search
None
See application file for complete search history.

(56) References Cited

U.S. PATENT DOCUMENTS

| | | |
|---|---|---|
| 3,892,722 A | 7/1975 | Babitsky et al. |
| 4,022,652 A | 5/1977 | Hirano et al. |
| 4,088,652 A | 5/1978 | Fanshawe et al. |
| 4,118,393 A | 10/1978 | Fanshawe et al. |
| 4,118,417 A | 10/1978 | Epstein |
| 4,131,611 A | 12/1978 | Fanshawe et al. |
| 4,196,120 A | 4/1980 | Fanshawe et al. |
| 4,231,935 A | 11/1980 | Fanshawe et al. |
| 4,336,268 A | 6/1982 | Bruderer et al. |
| 4,435,419 A | 3/1984 | Epstein et al. |
| 4,467,102 A | 8/1984 | Toda et al. |
| 4,504,657 A | 3/1985 | Bouzard et al. |
| 4,521,431 A | 6/1985 | Crookes |
| 4,591,598 A | 5/1986 | Urbach et al. |
| 5,039,680 A | 8/1991 | Imperato et al. |
| 5,075,341 A | 12/1991 | Mendelson et al. |
| 5,130,430 A | 7/1992 | Shaw |
| 5,198,459 A | 3/1993 | Imperato et al. |
| 5,232,934 A | 8/1993 | Downs |
| 5,488,056 A | 1/1996 | Bodick et al. |
| 5,556,837 A | 9/1996 | Nestler et al. |
| 5,556,838 A | 9/1996 | Mayer et al. |
| 5,574,052 A | 11/1996 | Rose et al. |
| 5,663,343 A | 9/1997 | van der Meij et al. |
| 5,672,360 A | 9/1997 | Sackler et al. |
| 5,762,925 A | 6/1998 | Sagen |
| 5,911,992 A | 6/1999 | Braswell et al. |
| 5,916,920 A | 6/1999 | Fernandez et al. |
| 5,969,156 A | 10/1999 | Briggs et al. |
| 5,985,864 A | 11/1999 | Imai et al. |
| 6,109,269 A | 8/2000 | Rise et al. |
| 6,121,261 A | 9/2000 | Glatt et al. |
| 6,194,000 B1 | 2/2001 | Smith et al. |
| 6,204,284 B1 | 3/2001 | Beer et al. |
| 6,245,357 B1 | 6/2001 | Edgren et al. |
| 6,245,911 B1 | 6/2001 | Imai et al. |
| 6,268,507 B1 | 7/2001 | Massey et al. |
| 6,333,428 B1 | 12/2001 | Nakazato et al. |
| 6,372,919 B1* | 4/2002 | Lippa et al. ................ 548/452 |
| 6,569,887 B2 | 5/2003 | Lippa et al. |
| 6,716,868 B2 | 4/2004 | Lippa et al. |
| 6,872,718 B1 | 3/2005 | Ohkawa et al. |

(Continued)

FOREIGN PATENT DOCUMENTS

| | | |
|---|---|---|
| AU | 519620 | 12/1981 |
| BE | 858683 | 3/1978 |

(Continued)

OTHER PUBLICATIONS

"Dimethylsulfide Borane (DMSB): Technical Data Sheet," BASF: The Chemical Company, Jan. 2004.*
U.S. Appl. No. 11/433,789, filed May 12, 2006, Lippa et al.
U.S. Appl. No. 11/438,909, filed May 22, 2006, Lippa et al.
U.S. Appl. No. 11/442,743, filed May 30, 2006, Lippa et al.
U.S. Appl. No. 11/445,950, filed Jun. 2, 2006, Russell et al.
Bernstein, J., "Crystal Structure Prediction and Polymorphism," ACA Transactions, 2004, 39, 14-23.
Braga, D. et al., "Dealing with Crystal Forms (The Kingdom of Serendip?)," Chemistry, An Asian Journal, 2011, 6, 2214-2223.
Brittain, H., Ed., Polymorphism in Pharmaceutical Solids, 1999, p. 238.

(Continued)

*Primary Examiner* — Alicia L Otton
(74) *Attorney, Agent, or Firm* — Hoxie & Associates LLC

(57) ABSTRACT

The present invention is concerned with novel processes for the preparation of (+)-1-(3,4-dichlorophenyl)-3-azabicyclo [3.1.0]hexane or a pharmaceutically acceptable salt thereof, and (−)-1-(3,4-dichlorophenyl)-3-azabicyclo[3.1.0]hexane or a pharmaceutically acceptable salt thereof. These compounds have pharmaceutical utility and are known to be useful for treating e.g., depression, anxiety disorders, eating disorders and urinary incontinence.

19 Claims, No Drawings

(56) References Cited

U.S. PATENT DOCUMENTS

| | | | |
|---|---|---|---|
| 7,041,835 | B2 | 5/2006 | Lippa et al. |
| 7,081,471 | B2 | 7/2006 | Lippa et al. |
| 7,094,799 | B2 | 8/2006 | Russell et al. |
| 7,098,229 | B2 | 8/2006 | Lippa et al. |
| 7,098,230 | B2 | 8/2006 | Lippa et al. |
| 2001/0034343 | A1 | 10/2001 | Maynard et al. |
| 2004/0102638 | A1 | 5/2004 | Russell et al. |
| 2004/0122017 | A1 | 6/2004 | Clader et al. |
| 2004/0127541 | A1 | 7/2004 | Codd et al. |
| 2004/0132797 | A1 | 7/2004 | Lippa et al. |
| 2004/0157869 | A1 | 8/2004 | Lippa et al. |
| 2004/0157870 | A1 | 8/2004 | Lippa et al. |
| 2004/0157908 | A1 | 8/2004 | Lippa et al. |
| 2005/0222146 | A1 | 10/2005 | Fryer et al. |
| 2006/0100263 | A1 | 5/2006 | Basile et al. |
| 2006/0173064 | A1 | 8/2006 | Lippa et al. |
| 2006/0223875 | A1 | 10/2006 | Skolnick et al. |
| 2007/0082938 | A1 | 4/2007 | Russell et al. |
| 2008/0009538 | A1 | 1/2008 | Skolnick |
| 2008/0027119 | A1 | 1/2008 | Lippa et al. |
| 2008/0269348 | A1 | 10/2008 | Skolnick et al. |
| 2008/0293822 | A1 | 11/2008 | Skolnick et al. |

FOREIGN PATENT DOCUMENTS

| | | | |
|---|---|---|---|
| BE | 893707 | | 12/1982 |
| EP | 0 444 855 | A1 | 9/1991 |
| JP | 58-13568 | A | 1/1983 |
| JP | 4-211638 | A | 8/1992 |
| JP | 9-183779 | A | 7/1997 |
| JP | 2000-159761 | A | 6/2000 |
| JP | 2000-256384 | A | 9/2000 |
| JP | 2000-336071 | A | 12/2000 |
| WO | WO 99/49857 | A1 | 10/1999 |
| WO | WO 03/047568 | | 6/2003 |
| WO | WO 2005/080382 | | 9/2005 |
| WO | WO 2006/023659 | | 3/2006 |
| WO | WO 2006/096810 | * | 9/2006 ............. A61K 31/40 |
| WO | WO 2006/108701 | | 10/2006 |
| WO | WO 2007/016155 | | 2/2007 |
| WO | WO 2007/022933 | | 3/2007 |
| WO | WO 2007/022934 | | 3/2007 |
| WO | WO 2007/022980 | | 3/2007 |
| WO | WO 2007/127421 | | 11/2007 |

OTHER PUBLICATIONS

Brittain, H., Ed., "Effects of Pharmaceutical Processing on Drug Polymorphs and Solvates" in Polymorphism in Pharmaceutical Solids, 1990, 95, 331-361.

Chawla, G. et al., "Challenges in Polymorphism of Pharmaceuticals," CRIPS, 2004, 5 (1), 4 pages.

Concise Encyclopedia Chemistry, Walter de Gruyter and Company, Berlin; New York, 1994, pp. 872-873.

DeLorenzo, C. et al., "SEP-225289 Serotonin and Dopamine Transporter Occupancy: A PET Study," The Journal of Nuclear Medicine, 2011, 52 (7), 1150-1155.

Dunitz, J., "Are Crystal Structures Predictable," Chemical Communications, 2003, 545-548.

English-language abstract for JP 2000-159761 from the European Patent Office website (http://worldwide.espacenet.com/publicationDetails/biblio?DB=EPODOC&II=1&ND=3&adjacent=true&locale=en_EP&FT=D&date=20000613&CC=JP&NR=2000159761A&KC=A), 2 pages, website accessed Jan. 14, 2014.

English-language abstract for JP 2000-256384 A from the European Patent Office website (http://worldwide.espacenet.com/publicationDetails/biblio?DB=EPODOC&II=1&ND=3&adjacent=true&locale=en_EP&FT=D&date=20000919&CC=JP&NR=2000256384A&KC=A), 2 pages, website accessed Jan. 14, 2014.

International Search Report for International Application No. PCT/US2005/029420, mailed Sep. 25, 2006, 2 pages.

International Preliminary Report on Patentability for International Application No. PCT/US2005/029420, Date of issuance of the report Feb. 20, 2007, 4 pages.

Learned, S. et al., "Efficacy, Safety, and Tolerability of a Triple Reuptake Inhibitor GSK372475 in the Treatment of Patients with Major Depressive Disorder: Two Randomized, Placebo- and Active-Controlled Clinical Trials," Journal of Psychopharmacology, 2012, 26 (5), 653-662.

Maddox, J., "Crystals from First Principles," Nature, 1988, 335, 201.

McArdle, P. et al., "A Method for the Prediction of the Crystal Structure of Ionic Organic Compounds—The Crystal Structures of O-Toluidinium Chloride and Bromide and Polymorphism of Bicifadine Hydrochloride," CrystEngComm, 2004, 6 (53), 303-309.

Newman, A. et al., "Solid-State Analysis of the Active Pharmaceutical Ingredient in Drug Products," Drug Discovery Today, 2003, 8 (19), 898-905.

Price, S., "The Computational Prediction of Pharmaceutical Crystal Structures and Polymorphism," Advanced Drug Delivery Reviews, 2004, 56, 301-319.

Sorbera, L. et al., "Bicifadine," Drugs of the Future, 2005, 30 (1), 7-10.

U.S. Pharmacopia #23, National Formulary #18, 1995, pp. 1843-1844.

Vishweshwar, P. et al., "The Predictably Elusive Form II of Aspirin," Journal of the American Chemical Society, 2005, 127, 16802-16803.

Welch, W. et al., "Nontricyclic Antidepressant Agents Derived from cis- and trans-1-Amino-4-aryltetralins," Journal of Medicinal Chemistry, 1984, 27, 1508-1515.

Bayés, M. et al., "Gateways to Clinical Trials," Methods and Findings in Experimental and Clinical Pharmacology, 2003, 25 (3), 225-248.

Beer, B. et al., "DOV 216,303, A 'Triple' Reuptake Inhibitor: Safety, Tolerability, and Pharmacokinetic Profile," Journal of Clinical Pharmacology, 2004, 44, 1360-1367.

Blum, K. et al., "Dopamine D2 Receptor Gene Variants: Association and Linkage Studies in Impulsive-Addictive-Compulsive Behaviour," Pharmacogenetics, 1995, 5, 121-141.

Bray, G., "A Concise Review on the Therapeutics of Obesity," Nutrition, 2000, 16, 953-960.

Caíra, M., "Crystalline Polymorphism of Organic Compounds," Topics in Current Chemistry, 1998, 198, 163-208, abstract only.

Casadio, S. et al., "Acide Phenyl-1-hydroxymethyl-2-cyclopropane Carboxylique Et Derives," Bollettino Chimico Farmaceutico, 1978, 117, 331-342.

Crown, W., "Economic Outcomes Associated with Tricyclic Antidepressant and Selective Serotonin Reuptake Inhibitor Treatments for Depression," Acta Psychiatrica Scandinavica, 2000, 101, 62-66.

Czobor, P. et al., "A Double-Blind, Placebo Controlled Randomized Study of DOV220,075 (Bicifadine) SR and Codeine 60 mg in the Treatment of Post-Operative Dental Pain," 2003, American Pain Society, Poster # 915, 2 pages.

Czobor, P. et al., "A Two Center Double-Blind, Placebo-Controlled Randomized Study of DOV 220,075 (Bicifadine) SR and Tramadol 100 mg in the Treatment of Post-Operative Dental Pain," Journal of Pain, 2004, 5 (3), Supplement 1, 59, 2 pages.

D'Aquila, P. et al., "The Role of Dopamine in the Mechanism of Action of Antidepressant Drugs," European Journal of Pharmacology, 2000, 405, 365-373.

Epstein, J. et al., "1-Aryl-3-azabicyclo[3.1.0]hexanes, A New Series of Nonnarcotic Analgesic Agents," Journal of Medicinal Chemistry, 1981, 24 (5), 481-490, abstract only.

Epstein, J. et al., "1-Aryl-3-azabicyclo[3.1.0]hexanes, A New Series of Nonnarcotic Analgesic Agents," Journal of Medicinal Chemistry, 1981, 24 (5), 481-490.

Epstein, J. et al., "Bicifadine: Non-Narcotic Analgesic Activity of 1-Aryl-3-azabicyclo[3.1.0]hexanes," NIDA Research Monograph, 1982, 41, 93-98.

Ettmayer, P. et al., "Lessons Learned from Marketed and Investigational Prodrugs," Journal of Medicinal Chemistry, 2004, 47 (10), 2393-2404.

(56) References Cited

OTHER PUBLICATIONS

Fauci, A. et al., Eds., Harrison's Principles of Internal Medicine, 14th Edition, vol. 1, McGraw-Hill, Health Professions Division, New York, 1998, pp. 2485-2503.

Frazer, A. "Norepinephrine Involvement in Antidepressant Action," Journal of Clinical Psychiatry, 2000, 61 (supplement 10), 25-30.

Fredman, S. et al., "Partial Response, Nonresponse, and Relapse with Selective Serotonin Reuptake Inhibitors in Major Depression: A Survey of Current 'Next-Step' Practices," Journal of Clinical Psychiatry, 2000, 61 (6), 403-408.

Goodman & Gilman's The Pharmacological Basis of Therapeutics, Ninth Edition, McGraw-Hill, Health Professions Division, New York, 1996, Chapter 18 entitled "Drugs and the Treatment of Psychiatric Disorders, Psychosis and Anxiety," by Ross J. Baldessarini, p. 399; Chapter 19 entitled "Drugs and the Treatment of Psychiatric Disorders, Depression and Mania," by Ross J. Baldessarini, pp. 431-459.

Grant, J., Ed., Hackh's Chemical Dictionary, Fourth Edition, McGraw-Hill Book Company, New York, 1969, pp. 474-475.

Hitri, A. et al., "Molecular, Functional and Biochemical Characteristics of the Dopamine Transporter: Regional Differences and Clinical Relevance," Clinical Neuropharmacology, 1994, 17 (1), 1-22.

Hoffman, B. et al., "Localization and Dynamic Regulation of Biogenic Amine Transporters in the Mammalian Central Nervous System," Frontiers in Neuroendocrinology, 1998, 19, 187-231.

International Search Report for International Application No. PCT/US2007/010288, Date of mailing of the International Search Report Oct. 12, 2007, 2 pages.

Kiyatkin, E., "Dopamine Mechanisms of Cocaine Addiction," International Journal of Neuroscience, 1994, 78, 75-101.

Kreek, M., "Cocaine, Dopamine and the Endogenous Opioid System," Journal of Addictive Diseases, 1996, 15 (4), 73-96.

Leonhardt, M. et al., "New Approaches in the Pharmacological Treatment of Obesity," European Journal of Nutrition, 1999, 38, 1-13.

Lima, L. et al., "Bioisosterism: A Useful Strategy for Molecular Modification and Drug Design," Current Medicinal Chemistry, 2005, 12, 23-49.

McBriar, M. et al., "Discovery of Bicycloalkyl Urea Melanin Concentrating Hormone Receptor Antagonists: Orally Efficacious Antiobesity Therapeutics," Journal of Medicinal Chemistry, 2005, 48, 2274-2277.

McBriar, M. et al., "Discovery of Orally Efficacious Melanin-Concentrating Hormone Receptor-1 Antagonists as Antiobesity Agents. Synthesis, SAR, and Biological Evaluation of Bicyclo[3.1.0]hexyl Ureas," Journal of Medicinal Chemistry, 2006, 49, 2294-2310.

McCardle, P. et al., "A Method for the Prediction of the Crystal Structure of Ionic Organic Compounds—The Crystal Structures of o-Toluidinium Chloride and Bromide and Polymorphism of Bicifadine Hydrochloride," CrystEngComm, 2004, 6 (53), 303-309.

McMillen, B. et al., "Effect of DOV 102,677 on the Volitional Consumption of Ethanol by Myers' High Ethanol-Preferring Rat," Alcoholism: Clinical and Experimental Research, 2007, 31 (11), 1866-1871.

Meyerson, L. et al., "Allosteric Interaction Between the Site Labeled by [$^3$H]Imipramine and the Serotonin Transporter in Human Platelets," Journal of Neurochemistry, 1987, 48, 560-565.

Morissette, S. et al., "High-throughput Crystallization: Polymorphs, Salts, Co-crystals and Solvates of Pharmaceutical Solids," Advanced Drug Delivery Reviews, 2004, 56, 275-300.

Nagatsu, T. et al., "Changes in Cytokines and Neurotrophins in Parkinson's Disease," Journal of Neural Transmission. Supplementa, 2000, 60, 277-290.

Noble, E., "Polymorphisms of the $D_2$ Dopamine Receptor Gene and Alcoholism and Other Substance Use Disorders," Alcohol & Alcoholism, 1994, Supplement 2, 35-43.

"Pain Therapeutics Takes Different Path, Improving Long-term Pain Relief by Reducing Dependency and Tolerance," Genetic Engineering & Biotechnology News, 2006, 26 (12), 2 pages.

Porter, E. et al., "Single Dose Comparison of Bicifadine, Codeine and Placebo in Postoperative Pain," Current Therapeutic Research, 1981, 30 (3), 156-160.

Scates, A. et al., "Reboxetine: A Selective Norepinephrine Reuptake Inhibitor for the Treatment of Depression," Annals of Pharmacotherapy, 2000, 34, 1302-1312.

Shuto, S. et al., "Synthesis of (+) and (−)-Milnaciprans and Their Conformationally Restricted Analogs," Tetrahedron Letters, 1996, 37 (5), 641-644.

Simon, G. et al., "TCAs or SSRIs as Initial Therapy for Depression?" The Journal of Family Practice, 1999, 48 (11), 845-846.

Skolnick, P., "Beyond Monoamine-Based Therapies: Clues to New Approaches," Journal of Clinical Psychiatry, 2002, 63, Supplement 2, 19-23.

Skolnick, P. et al., "Antidepressant-like Actions of DOV 21,947: A 'Triple' Reuptake Inhibitor," European Journal of Pharmacology, 2003, 461, 99-104.

Skolnick, P. et al., "'Broad Spectrum' Antidepressants: Is More Better for the Treatment of Depression," Life Sciences, 2003, 73, 3175-3179.

Stacy, M. et al., "Treatment Options for Early Parkinson's Disease," American Family Physician, 1996, 53 (4), 1281-1287.

Stella, V., "Prodrugs as Therapeutics," Expert Opinion on Therapeutic Patents, 2004, 14 (3), 277-280.

Sullivan, A. et al., "Mechanisms of Appetite Modulation by Drugs," Federation Proceedings, 1985, 44 (1), Part 1, 139-144.

Taylor, A. et al., "Scales for the Identification of Adults with Attention Deficit Hyperactivity Disorder (ADHD): A Systematic Review," Research in Developmental Disabilities, 2011, 32, 924-938.

Testa, B., "Prodrug Research: Futile or Fertile," Biochemical Pharmacology, 2004, 68, 2097-2106.

Theeuwes, F., "Drug Delivery Fuels Specialty Pharma, Rich Source of Innovation Now Significant Platform to Launch New Companies," Genetic Engineering and Biotechnology News, 2007, 27 (10), 2 pages.

Vippagunta, S. et al., "Crystalline Solids," Advanced Drug Delivery Reviews, 2001, 48, 3-26.

Wang, R. et al., "The Oral Analgesic Efficacy of Bicifadine Hydrochloride in Postoperative Pain," Journal of Clinical Pharmacology, 1982, 22, 160-164.

Wolff, M., Ed., Burger's Medicinal Chemistry and Drug Discovery, Fifth Edition, vol. I: Principles and Practice, A Wiley-Interscience Publication, John Wiley & Sons, Inc. New York, 1994, pp. 975-977.

Wong, E. et al., "Reboxetine: A Pharmacologically Potent, Selective, and Specific Norepinephrine Reuptake Inhibitor," Biological Psychiatry, 2000, 47, 818-829.

Xu, F. et al., "Stereocontrolled Synthesis of Trisubstituted Cyclopropanes: Expedient, Atom-Economical Asymmetric Syntheses of (+)-Bicifadine and DOV21947," Organic Letters, 2006, 4 pages, face of article indicates published on the web on Jul. 25, 2006.

Zhang, M. et al., "Studies on the Structure-Activity Relationship of Bicifadine Analogs as Monoamine Transporter Inhibitors," Bioorganic & Medicinal Chemistry Letters, 2008, 18, 3682-3686.

Byrn, S. et al., Solid-State Chemistry of Drugs, Second Edition, Stipes Publishing, Illinois, 1999, Chapter 11 entitled "Hydrates and Solvates," pp. 233-247.

International Preliminary Report on Patentability for International Application No. PCT/US2007/010288, Date of issuance of the report Oct. 28, 2008, 5 pages.

Korner, J. et al., "The Emerging Science of Body Weight Regulation and Its Impact on Obesity Treatment," The Journal of Clinical Investigation, 2003, 111 (5), 565-570.

Micheli, F. et al., "1-(Aryl)-6-[alkoxyalkyl]-3-azabicyclo[3.1.0]hexanes and 6-(Aryl)-6-[alkoxyalkyl]-3-azabicyclo[3.1.0]hexanes: A New Series of Potent and Selective Triple Reuptake Inhibitors," Journal of Medicinal Chemistry, 2010, 53, 2534-2551.

(56) References Cited

OTHER PUBLICATIONS

Rouhi, A., "The Right Stuff, From Research and Development to the Clinic, Getting Drug Crystals Right is Full of Pitfalls," Chemical & Engineering News, 2003, 81 (8), 32-35.

Written Opinion of the International Searching Authority for International Application No. PCT/US2007/010288, Date of mailing Oct. 12, 2007, 4 pages.

Xu, F. et al., Supporting Information for "Stereocontrolled Synthesis of Trisubstituted Cyclopropanes: Expedient, Atom-Economical, Asymmetric Syntheses of (+)-Bicifadine and DOV21947," Organic Letters, 2006, S1-S14, available at: pubs.acs.org/doi/suppl/10.1021/ol061650w/suppl_file/ol061650wsi20060705_100050.pdf.

Xu, F. et al., Supporting Information for "Stereocontrolled Synthesis of Trisubstituted Cyclopropanes: Expedient, Atom-Economical, Asymmetric Syntheses of (+)-Bicifadine and DOV21947," Organic Letters, 2006, 11 pages, available at: pubs.acs.org/doi/suppl/10.1021/ol061650w/suppl_file/ol061650wsi20060707_052859.pdf.

Xu, F. et al., "Chlorination/Cyclodehydration of Amino Alcohols with $SOCl_2$: An Old Reaction Revisited," Journal of Organic Chemistry, 2008, 73, 312-315.

Xu, F. et al., Supporting Information for "Chlorination/Cyclodehydration of Amino Alcohols with $SOCl_2$: An Old Reaction Revisited," Journal of Organic Chemistry, 2008, S1-S32, available at: pubs.acs.org/doi/suppl/10.1021/jo701877h/suppl_file/jo701877h-file003.pdf.

U.S. Appl. No. 60/702,800, filed Jul. 26, 2005, Lippa, et al.

U.S. Appl. No. 60/703,364, filed Jul. 27, 2005, Skolnick, et al.

Express Pharma Pulse, "Polymorphism of pharmaceuticals: Challenges and Opportunities" Express-Pharma-Online, Oct. 23, 2003, pp. 1-3, http://archivepharma.financialexpress.com/20031023/edit02/shtml.

Shuto, et al., "Synthesis of Conformationally Restricted Analogs of Baclofen, a Potent $GABA_b$ Receptor Agonist, by the Introduction of a Cyclopropane Ring" Chem. Pharm. Bull., (Aug. 1999) vol. 47(8), 1188-1192.

\* cited by examiner

PROCESS FOR THE SYNTHESIS OF (+) AND (−)-1-(3,4-DICHLOROPHENYL)-3-AZABICYCLO[3.1.0]HEXANE

CROSS REFERENCE TO RELATED APPLICATIONS

This application is a continuation of U.S. patent application Ser. No. 13/366,211 filed Feb. 3, 2012, now abandoned, which is a continuation of U.S. patent application Ser. No. 13/207,279 filed Aug. 10, 2011, now abandoned, which is a continuation of U.S. patent application Ser. No. 12/782,705 filed May 18, 2010, now abandoned, which is a continuation of U.S. patent application Ser. No. 11/740,667 filed Apr. 26, 2007, now abandoned, which claims priority to U.S. Provisional Application No. 60/796,097 filed Apr. 28, 2006, the contents of each of which are incorporated herein by reference.

JOINT RESEARCH AGREEMENT

The claimed invention was made by or on behalf of the below listed parties to a joint research agreement, which was in effect on or before the date the claimed invention was made, and the claimed invention was made as a result of activities undertaken within the scope of the joint research agreement. The parties to the joint research agreement were MSD Warwick (Manufacturing) Ltd. and DOV Pharmaceutical, Inc.

BACKGROUND OF THE INVENTION

The present invention relates to processes for the preparation of (+)-1-(3,4-dichlorophenyl)-3-azabicyclo[3.1.0]hexane or a pharmaceutically acceptable salt thereof, and (−)-1-(3,4-dichlorophenyl)-3-azabicyclo[3.1.0]hexane or a pharmaceutically acceptable salt thereof. These compounds are known to be useful for treating e.g., depression, anxiety disorders, eating disorders and urinary incontinence (see U.S. Pat. Nos. 6,372,919, 6,569,887 and 6,716,868).

The general processes disclosed in the art for the preparation of racemic, (+)-1-(3,4-dichlorophenyl)-3-azabicyclo[3.1.0]hexane and (−)-1-(3,4-dichlorophenyl)-3-azabicyclo[3.1.0]hexane result in relatively low and inconsistent yields of the desired product (see e.g., U.S. Pat. Nos. 4,118,417, 4,131,611, 4,196,120, 4,231,935, 4,435,419, 6,372,919, 6,569,887, 6,716, 868: Sorbera, et al., *Drugs Future* 2005, 30, 7; and Epstein, et al., *J. Med. Chem.*, 1981, 24, 481). Some of such processes rely on the use of expensive reagents. In contrast to the previously known processes, the present invention provides effective methodology for the preparation of (+) or (−)-1-(3,4-dichlorophenyl)-3-azabicyclo[3.1.0]hexane in relatively high yield and enantiomeric purity. It will be appreciated that (+) and (−)-1-(3,4-dichlorophenyl)-3-azabicyclo[3.1.0]hexane are useful therapeutic agents. As such, there is a need for the development of processes for the preparation of (+) and (−)-1-(3,4-dichlorophenyl)-3-azabicyclo[3.1.0]hexane which are readily amenable to scale-up, use cost-effective and readily available reagents, and which are therefore capable of practical application to large scale manufacture. Accordingly, the subject invention provides a process for the preparation of (+) and (−)-1-(3,4-dichlorophenyl)-3-azabicyclo[3.1.0]hexane via a very simple, short and highly efficient synthesis.

SUMMARY OF THE INVENTION

The novel processes of this invention involves the asymmetric synthesis of (+)-1-(3,4-dichlorophenyl)-3-azabicyclo[3.1.0]hexane and (−)-1-(3,4-dichlorophenyl)-3-azabicyclo[3.1.0]hexane. In particular, the present invention provides novel processes for the preparation of a compound of the formula I:

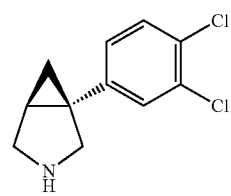

or a pharmaceutically acceptable salt thereof, or a compound of the formula Ib:

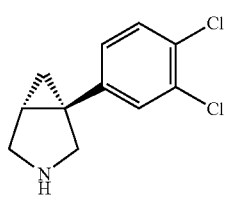

or a pharmaceutically acceptable salt thereof.

DETAILED DESCRIPTION OF THE INVENTION

The present invention is directed to a process for preparing a compound of the formula I:

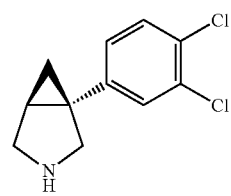

or a pharmaceutically acceptable salt thereof, comprising:

contacting 3,4-dichlorophenylacetonitrile and (S)-epichlorohydrin of the formula:

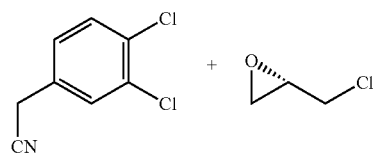 [SMILES: N#CCc1ccc(Cl)c(Cl)c1 ; ClC[C@@H]1CO1]

in the presence of a base, to give cyclopropyl compounds of the formula II:

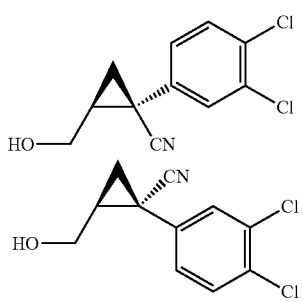

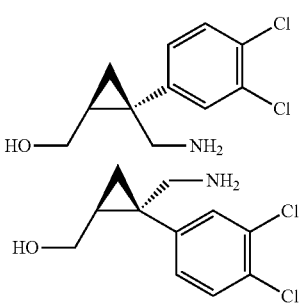

followed by reducing the compounds of formula II with a reducing agent to give amino alcohol compounds of the formula III:

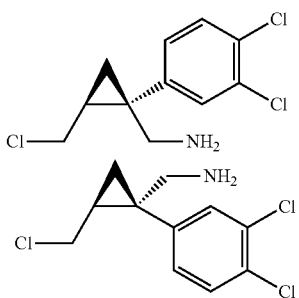

followed by chlorinating the compounds of formula III with a chlorinating agent to give chloro compounds of the formula IV:

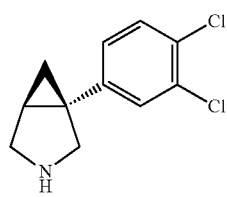

followed by cyclodehydration of the compounds of the formula IV with a base to give the compound of formula I, or a pharmaceutically acceptable salt thereof.

The present invention is further directed to a process for preparing a compound of the formula I:

I or a pharmaceutically acceptable salt thereof, comprising:
cyclodehydration of the compound of the formula IV-1:

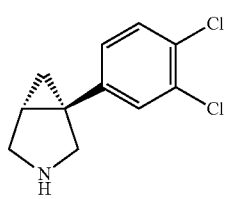

with a base to give the compound of formula I, or a pharmaceutically acceptable salt thereof.

The present invention is further directed to a process for preparing a compound of the formula Ib:

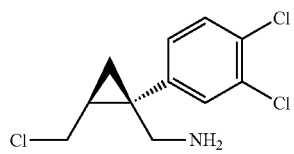

or a pharmaceutically acceptable salt thereof, comprising:
contacting 3,4-dichlorophenylacetonitrile and (R)-epichlorohydrin of the formula:

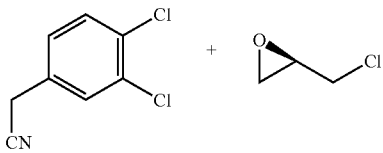 [SMILES: N#CCc1ccc(Cl)c(Cl)c1 ; ClC[C@H]1CO1]

in the presence of a base, to give cyclopropyl compounds of the formula IIb:

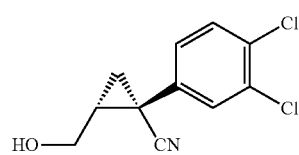

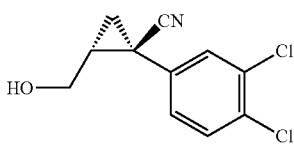

followed by reducing the compounds of formula IIb with a reducing agent to give amino alcohol compounds of the formula IIIb:

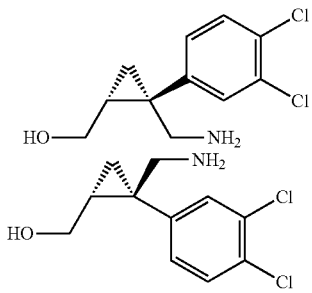

followed by chlorinating the compounds of formula IIIb with a chlorinating agent to give chloro compounds of the formula IVb:

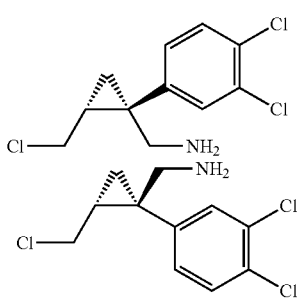

followed by cyclodehydration of the compounds of the formula IVb with a base to give the compound of formula Ib, or a pharmaceutically acceptable salt thereof.

The present invention is further directed to a process for preparing a compound of the formula Ib:

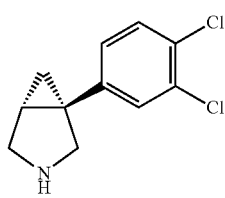

or a pharmaceutically acceptable salt thereof comprising: cyclodehydration of the compound of the formula IVb-2

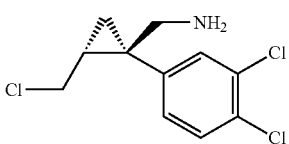

with a base to give the compound of formula Ib, or a pharmaceutically acceptable salt thereof.

In an embodiment of the present invention the step of contacting 3,4-dichlorophenylacetonitrile and (S)-epichlorohydrin [or (R)-epichlorohydrin] in the presence of a base to give cyclopropyl compounds of the formula II [or IIb], the base may be selected from sodium hexamethyldisilazide (NaHMDS), potassium hexamethyldisilazide (KHMDS), lithium hexamethyldisilazide (LiHMDS), potassium t-butoxide, potassium t-pentoxide, potassium amylate, lithium diisopropylamide (LDA), lithium tetramethylpiperidide (LiTMP), sec-butyllithium, or tert-butyllithium. Within this embodiment, the base is selected from sodium hexamethyldisilazide (NaHMDS), potassium hexamethyldisilazide (KHMDS) and lithium hexamethyldisilazide (LiHMDS). Further within this embodiment, the base is sodium hexamethyldisilazide (NaHMDS). Solvents for conducting the step of contacting 3,4-dichlorophenylacetonitrile and (S)-epichlorohydrin [or (S)-epichlorohydrin] in the presence of a base to give cyclopropyl compounds of the formula II [or IIb] comprise an organic solvent. Within this embodiment, the organic solvent comprises toluene, tetrahydrofuran (THF), diethyl ether, diglyme, dimethoxyethane (DME), or methyl t-butyl ether. Further within this embodiment, the organic solvent is tetrahydrofuran. The step of contacting 3,4-dichlorophenyl-acetonitrile and (S)-epichlorohydrin [or (S)-epichlorohydrin] in the presence of a base to give cyclopropyl compounds of the formula II [or IIb] is typically carried out at a temperature range of between about −30 and about 25° C. Within this embodiment, the temperature range is less than about 0° C. Further within this embodiment, the temperature range is between about −20 and about −5° C.

In an embodiment of the present invention the step of reducing of the compounds of formula II [or IIb] with a reducing agent to give amino alcohol compounds of the formula III [or IIIb], the reducing agent may be selected from borane dimethyl sulfide complex, borane tetrahydrofuran complex, sodium borohydride-borontrifluoride etherate, a dialkylborane, 9-borabicyclo[3.3.1]nonane (9-3BBN), and lithium aluminum hydride (LAH). Further within this embodiment, the reducing agent is borane dimethyl sulfide complex. Solvents for conducting the step of reducing of the compounds of formula II with a reducing agent to give amino alcohol compounds of the formula III [or IIIb] comprise an organic solvent. Within this embodiment, the organic solvent comprises toluene, tetrahydrofuran (THF), diethyl ether, diglyme, dimethoxyethane (DME), or methyl t-butyl ether. Further within this embodiment, the organic solvent is tetrahydrofuran. The step of reducing of the compounds of formula II [or IIb] with a reducing agent to give amino alcohol compounds of the formula III [or IIIb] is typically carried out at a temperature range of between about −30 and about 25° C. Within this embodiment, the temperature range is less than about 0° C. Further within this embodiment, the temperature range is between about −20 and about −5° C.

In an embodiment of the present invention the step of chlorinating the compounds of formula III [or IIIb] with a chlorinating agent to give chloro compounds of the formula IV [or IVb], the chlorinating agent may be selected from thionyl chloride, $SO_2Cl_2$, and $Ph_3P/CCl_4$. Further within this embodiment, the chlorinating agent is thionyl chloride. Solvents for conducting the step of chlorinating the compounds of formula III [or IIIb] with a chlorinating agent to give chloro compounds of the formula IV [or IVb] comprise an organic solvent. Within this embodiment, the organic solvent comprises toluene, tetrahydrofuran (THF), diethyl ether, diglyme, dimethoxyethane (DME), methyl t-butyl ether, ethyl acetate, isopropyl acetate or N-methyl pyrrolidinone. Further within this embodiment, the organic solvent comprises tetrahydrofuran, dimethoxyethane and isopropyl acetate. The step of chlorinating the compounds of formula III [or IIIb] with a chlorinating agent to give chloro compounds of the formula IV [or IVb] is typically carried out at a temperature range of between about 0 and about 40° C. Within this embodiment, the temperature range is less than about 0° C. Further within this embodiment, the temperature is about 25° C.

In an embodiment of the present invention the step of cyclodehydration of the compounds of the formula IV [or IVb] with a base to give the compound of formula [or Ib], the base may be selected from sodium hydroxide, potassium hydroxide, potassium bicarbonate, sodium bicarbonate, potassium carbonate, sodium carbonate, $Et_3N$, i-$Pr_2NEt$, DABCO, DBU, or other amine bases. Further within this embodiment, the base is sodium hydroxide. Solvents for conducting the step of cyclodehydration of the compounds of the formula IV [or IVb] with a base to give the compound of formula I [or Ib] comprise an aqueous solvent. In the step of cyclodehydration of the compounds of the formula IV [or IVb] with a base to give the compound of formula I [or Ib], the pH is typically at a range of between about 7-10. Within this embodiment, the pH is about 8-10. Further within this embodiment, the pH is about 8.5-9.5.

In an embodiment of the invention, the process steps are conducted sequentially without isolation of the intermediate compounds.

In a further embodiment, the present invention is directed to a process for the preparation of (+)-1-(3,4-dichlorophenyl)-3-azabicyclo[3.1.0]hexane as depicted below:

In a further embodiment, the present invention is directed to a process for the preparation of (+)-1-(3,4-dichlorophenyl)-3-azabicyclo[3.1.0]hexane as depicted below:

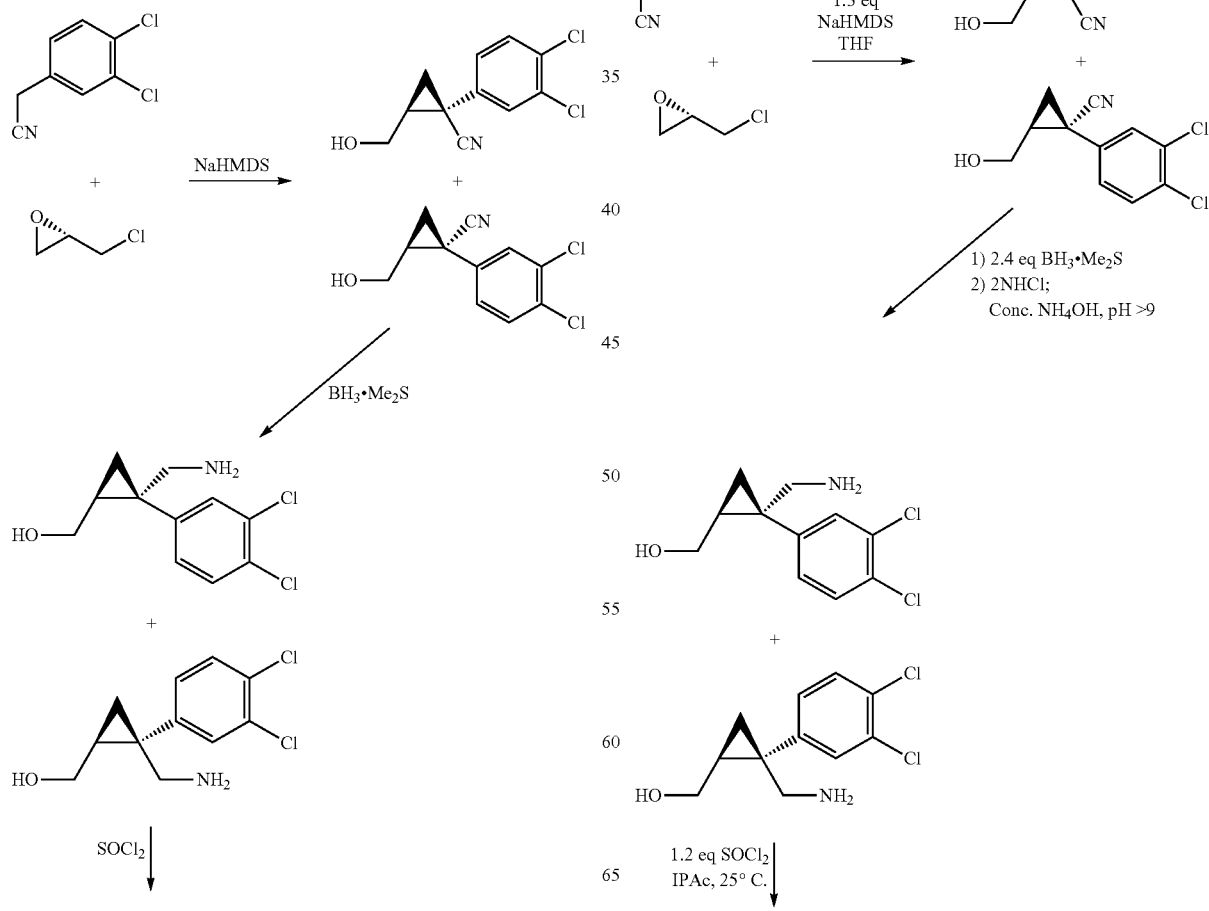

-continued

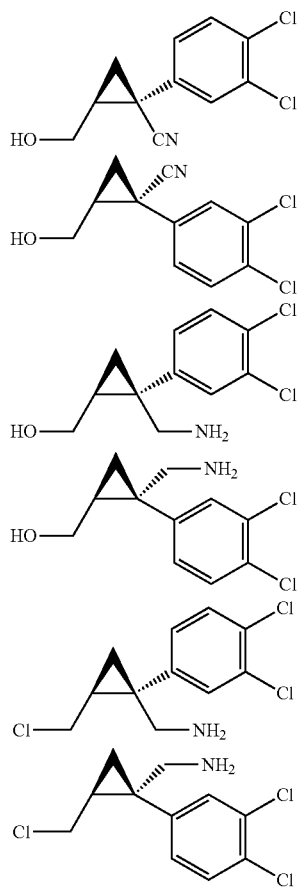

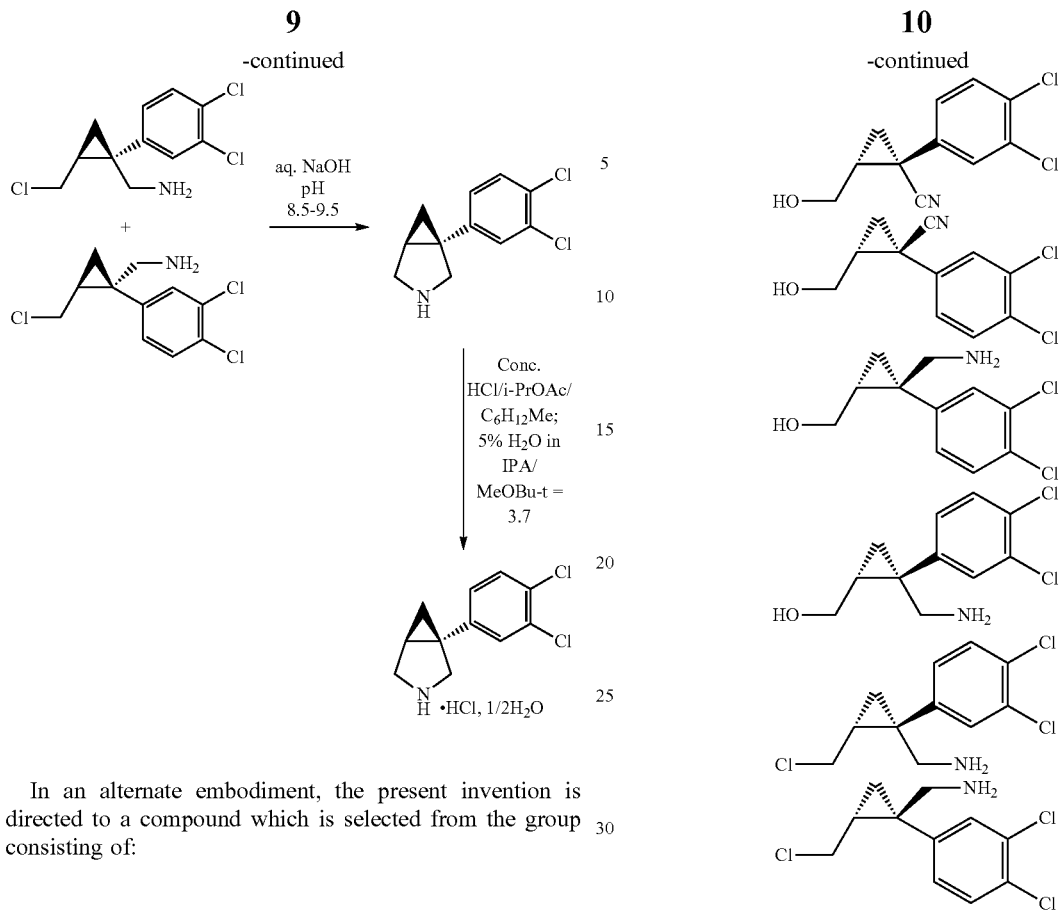

or a salt thereof.

The present invention provides a heavy metal-free synthesis that is efficient and atom economic so that (+)-1-(3,4-dichlorophenyl)-3-azabicyclo[3.1.0]hexane or (−)-1-(3,4-dichlorophenyl)-3-azabicyclo[3.1.0]hexane may be prepared via a single through process without requiring isolation of any intermediates. Starting from inexpensive, commercially available 3,4-dichlorophenylacetonitrile and (S)-epichlorohydrin (or (R)-epichlorohydrin), the key cyclopropane intermediate is constructed. Without further workup, the crude reaction mixture is reduced with borane dimethyl sulfide complex in one pot to afford the amino alcohol intermediates. The desired cis amino alcohol is directly cylodehydrated to give (+)-1-(3,4-dichlorophenyl)-3-azabicyclo[3.1.0]hexane or (−)-1-(3,4-dichlorophenyl)-3-azabicyclo[3.1.0]-hexane. The whole synthesis may be conducted as a single stage through process to allow direct isolation of (+)-1-(3,4-dichlorophenyl)-3-azabicyclo[3.1.0]hexane HCl salt or (−)-1-(3,4-dichlorophenyl)-3-azabicyclo[3.1.0]hexane HCl salt.

Another aspect of this invention is directed to the foregoing precesses wherein the (−)-1-(3,4-dichlorophenyl)-3-azabicyclo[3.1.0]hexane, or a pharmaceutically acceptable salt thereof, is present in an enantiomeric purity (enantiomeric excess) of greater than 90%, greater than 95%, greater than 98%, greater than 99%, greater than 99.5% (enantiomeric excess) or greater than 99.9% (enantiomeric excess).

Another aspect of this invention is directed to the foregoing precesses wherein the (−)-1-(3,4-dichlorophenyl)-3-azabicyclo[3.1.0]hexane, or a pharmaceutically acceptable salt thereof, is present in an enantiomeric purity (enantiomeric excess) of greater than 90%, greater than 95%, greater than 98%, greater than 99%, greater than 99.5% (enantiomeric excess) or greater than 99.9% (enantiomeric excess).

The term "pharmaceutically acceptable salts" refers to salts prepared from pharmaceutically acceptable non-toxic acids including inorganic or organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Specific acids include citric, hydrobromic, hydrochloric, maleic, phosphoric, sulfuric, fumaric, and tartaric acids. A specific acid is hydrochloric acid.

The present process is surprisingly efficient, minimizing the production of side products, and increasing productivity and purity. The starting materials and reagents for the subject processes are either commercially available or are known in the literature or may be prepared following literature methods described for analogous compounds. The skills required in carrying out the reaction and purification of the resulting reaction products are known to those in the art. Purification procedures include crystallization, distillation, normal phase or reverse phase chromatography.

The following examples are provided for the purpose of further illustration only and are not intended to be limitations on the disclosed invention. Unless otherwise noted, all reactions were conducted under $N_2$ atmosphere using standard air-free manipulation techniques. Solvents were purchased from Fisher Scientific Company and used without further purification. Commercial reagents were purchased either from Aldrich or Bayer and used without further purification. High performance liquid chromatography (HPLC) analysis was performed using Agilent Technology 1100 series instrument with ACE 5 C18 (240×4.6 mm ID., 5 μm particle size) column. Proton nuclear magnetic resonance ($^1$H NMR) spectra were measured on Bruker Avance-400 instrument (400 MHz). Carbon nuclear magnetic resonance ($^{13}$C NMR) spectra were measured on Bruker Avance-400 instrument (100 MHz) with complete proton decoupling. Chemical shifts are reported in ppm downfield from tetramethylsilane (TMS).

Example 1

(1R,5S)-(+)-1-(3,4-Dichlorophenyl)-3-azabicyclo[3,10]hexane

To a solution of 3,4-dichlorophenylacetonitrile (3.50 kg) and S-(+)-epichlorohydrin (2.22 kg) in THF (18.5 L) at −15° C. under atmosphere of $N_2$ was added NaHMDS (16.5 L, 2M in THF) dropwise over 3 h. The reaction mixture was stirred for 3 h at −15° C., then, overnight at −5° C. $BH_3$-$Me_2$S (neat, 10M, 4.4 L) was added over 2 h. The reaction mixture was then gradually warmed to 40° C. over 3 h. After aging 1.5 h at 40° C., the reaction mixture was cooled to 20-25° C. and slowly quenched into a 2N HCl solution (27.7 L). The quenched mixture was then aged for 1 h at 40° C. Concentrated $NH_4OH$ (6.3 L) was added and the aqueous layer was discarded. i-PrOAc (18.5 L) and 5% dibasic sodium phosphate (18.5 L) were charged. The organic phase was then washed with saturated brine (18.5 L), azetropically dried and solvent-switched to i-PrOAc (ca. 24.5 L) in vacuum.

The above crude amino alcohol solution in i-PrOAc was slowly subsurface-added to a solution of $SOCl_2$ (22.1 mol, 1.61 L) in i-PrOAc (17.5 L) at ambient temperature over 2 h. After aging additional 1-5 h, 5.0 N NaOH (16.4 L) was added over 1 h while the batch temperature was maintained at <30° C. with external cooling. The two-phase reaction mixture was stirred for 1 h at ambient temperature to allow pH to stabilize (usually to 8.5-9.0) with NaOH pH titration. The organic phase was washed with 40% aqueous i-PrOH (21 L) followed by water (10.5 L). Conc. HCl (1.69 L) was added. The aqueous i-PrOAc was azeotropically concentrated in vacuum to ca. 24.5 L. Methylcyclohexane (17.5 L) was added dropwise over 2 h. The wet cake was displacement-washed with 7 L of 40% methylcyclohexan/i-PrOAc followed by a slurry wash (7 L, i-PrOAc) and a displacement wash (7 L, i-PrOAc). Typical isolated yield: 57-60% corrected with wt %: 87-99.5% (based on HCl salt).

(1R,5S)-(+)-1-(3,4-Dichlorophenyl)-3-azabicyclo[3,10]hexane HCl salt (5.0 kg) was dissolved in i-PrOH (14.25 L) and water (0.75 L) at 55° C. Seeds (50 g) were added at 48-50° C. The batch was allowed to cool to ambient temperature (20° C.) over 2-4 h. MeOBu-t (37 L) was added dropwise over 2 h. After aging 1 h at 20° C., the batch was filtered. The wet cake was displacement-washed with 10 L of 30% i-PrOH in MeOBu-t followed by 2×7.5 L 10% i-PrOH in MeOBu-t (slurry wash, then displacement wash). The wet cake was suction dried under $N_2$ (10-50 RH %) at ambient temperature to give the hemihydrate HCl salt of (1R,5S)-(+)-1-(3,4-dichlorophenyl)-3-azabicyclo[3,10]hexane. Typical yield: 92%. $^1$H-NMR (400 MHz, $d_4$-MeOH): δ 7.52 (d, J=2.2 Hz, 1H), 7.49 (d, J=8.4 Hz, 1H), 7.26 (dd, J=2.1, 8.4 Hz, 1H), 3.78 (d, J=11.4 Hz, 1H), 3.69 (dd, J=3.9, 11.3 Hz, 1H), 3.62 (dd, J=1.4, 11.3 Hz, 1H), 3.53 (d, J=11.4 Hz, 1H), 2.21 (m, 1H), 1.29 (t, J=7.5 Hz, 1H), 1.23 (dd, J=4.9, 6.5 Hz, 1H). $^{13}$C-NMR (100 MHz, $d_4$-MOH): δ 141.0, 133.7, 132.2, 132.0, 130.6, 128.4, 51.7, 49.1, 31.8, 24.9, 16.5, Anal. Calcd for $C_{11}H_{13}Cl_3NO_{0-5}$: C, 48.29; H, 4.79; N, 5.12; Cl, 38.88. Found: C, 48.35; H, 4.87: N, 5.07; 38.55.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A process for preparing a compound of the formula I:

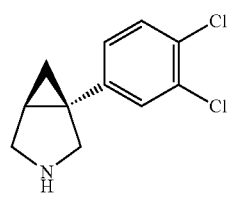

or a pharmaceutically acceptable salt thereof, comprising:

contacting 3,4-dichlorophenylacetonitrile and (S)-epichlorohydrin of the formula:

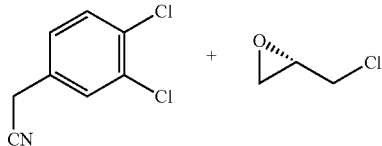 [SMILES: N#CCc1ccc(Cl)c(Cl)c1 ; ClC[C@@H]1CO1]

in the presence of a base, to give cyclopropyl compounds of the formula II:

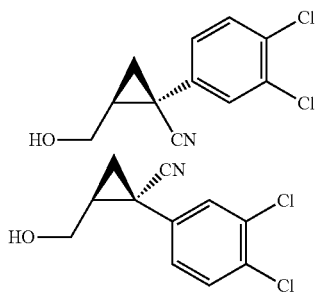

followed by reducing the compounds of formula II with a reducing agent to give amino alcohol compounds of the formula III:

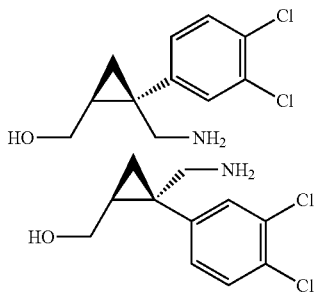

followed by chlorinating the compounds of formula III with a chlorinating agent to give chloro compounds of the formula IV:

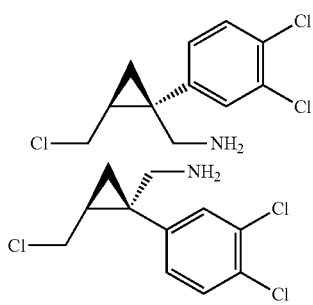

followed by cyclodehydration of the compounds of the formula IV with a base to give the compound of formula I, or a pharmaceutically acceptable salt thereof.

2. A process for preparing a compound of the formula I:

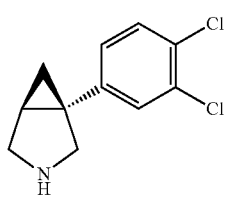

or a pharmaceutically acceptable salt thereof, comprising: cyclodehydration of the compound of the formula IV-I:

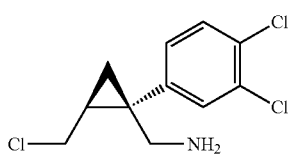

with a base to give the compound of formula I, or a pharmaceutically acceptable salt thereof.

3. The process of claim 1 wherein the step of contacting 3,4-dichlorophenyl-acetonitrile and (S)-epichlorohydrin in the presence of a base to give cyclopropyl compounds of the formula II, the base is selected from sodium hexamethyldisilazide (NaHMDS), potassium hexamethyldisilazide (KHMDS), lithium hexamethyldisilazide (LiHMDS), potassium t-butoxide, potassium t-pentoxide, potassium amylate, lithium diisopropylamide (LDA), lithium tetramethylpiperidide (LiTMP), sec-butyllithium, and tert-butyllithium.

4. The process of claim 3 wherein the base is selected from sodium hexamethyldisilazide (NaHMDS), potassium hexamethyldisilazide (KHMDS) and lithium hexamethyldisilazide (LiHMDS).

5. The process of claim 4 wherein the base is sodium hexamethyldisilazide (NaHMDS).

6. The process of claim 1 wherein the step of reducing of the compounds of the formula II with a reducing agent to give amino alcohol compounds of the formula III, the reducing agent is selected from borane dimethyl sulfide complex, borane tetrahydrofuran complex, sodium borohydride-borontrifluoride etherate, a dialkylborane, 9-borabicyclo[3.3.1]-nonane (9-BBN), and lithium aluminum hydride (LAH).

7. The process of claim 6 wherein the reducing agent is borane dimethyl sulfide complex.

8. The process of claim 1 wherein the step of chlorinating the compounds of the formula III with a chlorinating agent to give chloro compounds of the formula IV, the chlorinating agent is selected from thionyl chloride, $SO_2Cl_2$, and $Ph_3P/CCl_4$.

9. The process of claim 8 wherein the chlorinating agent is thionyl chloride.

10. The process of claim 1 wherein the step of cyclodehydration of the compounds of the formula IV with a base to give the compound of formula I, the base is selected from sodium hydroxide, potassium hydroxide, potassium bicarbonate, sodium bicarbonate, potassium carbonate, sodium carbonate, $Et_3N$, i-$Pr_2NEt$, DABCO and DBU.

11. The process of claim 10 wherein the base is sodium hydroxide.

12. The process of claim 1 wherein the steps are conducted sequentially without isolation of the compounds of formula II, formula III, or formula IV.

13. The process of claim 1, further comprising isolating the compound of formula I or a pharmaceutically acceptable salt thereof.

14. The process of claim 1, further comprising isolating a pharmaceutically acceptable salt of formula I.

15. The process of claim 2, further comprising isolating the compound of formula I or a pharmaceutically acceptable salt thereof.

16. The process of claim 2, further comprising isolating a pharmaceutically acceptable salt of formula I.

17. The process of claim 2, wherein the compound of the formula IV-I is prepared by chlorinating compounds of formula III:

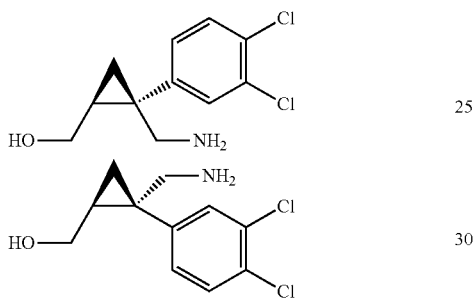

with a chlorinating agent.

18. A compound which is selected from the group consisting of:

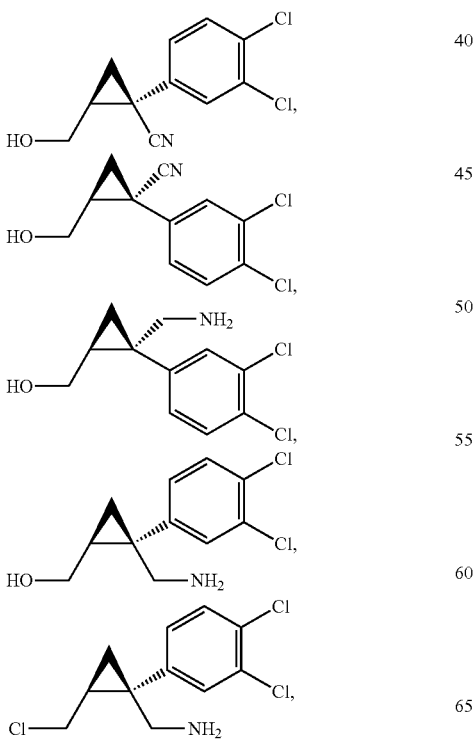

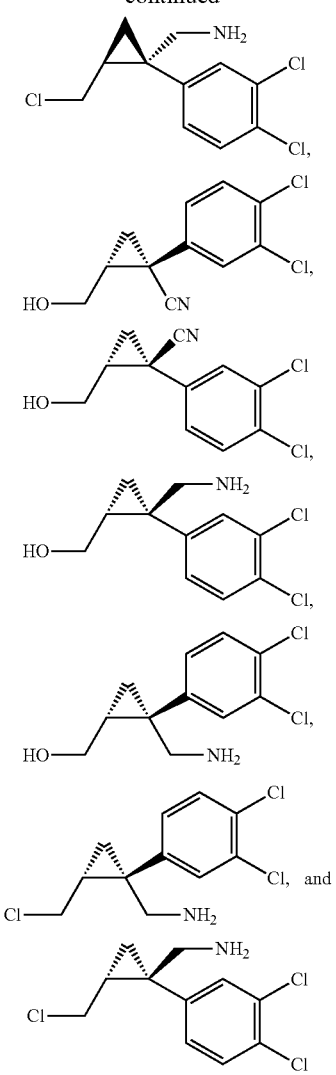

or a salt thereof.

19. A compound which is selected from the group consisting of:

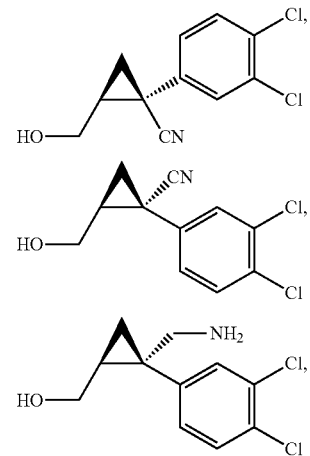

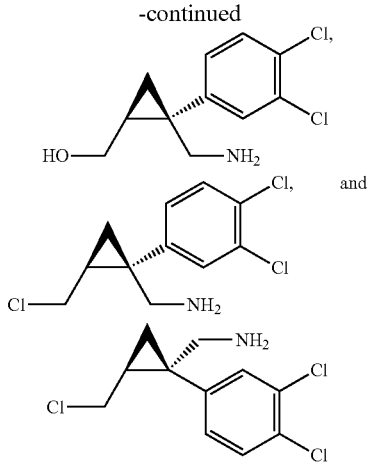
or a salt thereof.